US006526805B1

(12) United States Patent
Babes-Dornea et al.

(10) Patent No.: US 6,526,805 B1
(45) Date of Patent: Mar. 4, 2003

(54) APPARATUS FOR CONTINUOUSLY DETERMINING VOLATILE SUBSTANCES DISSOLVED IN INSULATING FLUID

(75) Inventors: Elena Babes-Dornea, Pierrefonds (CA); Claude Beauchemin, Valleyfield (CA); Bruno Georges, Ste. Genevieve (CA); Renyan Qin, Pierrefonds (CA); Jean-Christophe Marusic, Montreal (CA)

(73) Assignee: General Electric Co., Schenectady, NY (US)

( * ) Notice: Subject to any disclaimer, the term of this patent is extended or adjusted under 35 U.S.C. 154(b) by 0 days.

(21) Appl. No.: 09/637,083

(22) Filed: Aug. 11, 2000

(51) Int. Cl.[7] .......................... G01N 37/00; B01D 53/22
(52) U.S. Cl. .......................... 73/19.12; 73/31.07; 96/5; 95/46
(58) Field of Search .............................. 73/19.12, 31.07; 96/5; 95/46

(56) References Cited

U.S. PATENT DOCUMENTS

| 3,735,127 | A | * | 5/1973 | Astheimer | 250/346 |
|---|---|---|---|---|---|
| 4,384,207 | A | * | 5/1983 | Doctor | 250/349 |
| 4,484,936 | A | * | 11/1984 | Sakai | 96/6 |
| 5,054,328 | A | * | 10/1991 | Long et al. | 73/31.07 |
| 5,413,763 | A | * | 5/1995 | Jeffers | 96/6 |
| 5,599,179 | A | * | 2/1997 | Lindner et al. | 431/12 |
| 5,749,942 | A | * | 5/1998 | Mattis et al. | 96/6 |
| RE36,277 | E | * | 8/1999 | Black et al. | 250/339.13 |
| 6,003,362 | A | * | 12/1999 | Dieckmann et al. | 73/19.12 |
| 6,037,592 | A | * | 3/2000 | Sunshine et al. | 250/343 |
| 6,217,634 | B1 | * | 4/2001 | Dominelli et al. | 96/6 |

FOREIGN PATENT DOCUMENTS

JP         09089662 A    *  9/1995

* cited by examiner

Primary Examiner—Hezron Williams
Assistant Examiner—Michael Cygan
(74) Attorney, Agent, or Firm—Nixon & Vanderhye P.C.

(57) ABSTRACT

An apparatus and method are provided for continuously monitoring the operation of electrical equipment and preventing critical operational failures. The invention quantitatively determines the concentrations of gas and/or vapor (including water) components in an insulating fluid on a real time basis. An increase of one or more detected chemical components signifies an actual or potential electrical problem with the equipment. The preferred apparatus consists of a gas extractor, an infrared gas analysis instrument, and a gas diaphragm pump. Gas and water vapor components are extracted from the insulating fluid by permeating through a membrane in a gas extractor. The gas and/or vapor components are then brought into an infrared gas analyzer by the gas diaphragm pump. A quad detector in the analysis instrument identifies and determines the concentration of three specified gases and/or the vapor simultaneously.

22 Claims, 1 Drawing Sheet

APPARATUS FOR CONTINUOUSLY DETERMINING VOLATILE SUBSTANCES DISSOLVED IN INSULATING FLUID

BACKGROUND OF THE INVENTION

The present invention relates to a method for continuously detecting and monitoring the presence of volatile gases in oils and other fluids used to insulate electrical equipment. In particular, the invention relates to a method for quantitatively determining the specific concentration of certain gases, particularly hydrocarbons, dissolved in insulating fluids on a continuous, real time basis in order to evaluate the operation of the electrical devices while the equipment is still in operation. The invention also relates to an apparatus for simultaneously measuring the concentrations of several different gas components dissolved in an insulating fluid and/or the vapor phase constituents on a continuous, real time basis.

Oil-filled equipment, such as transformers, shunt reactors, current transformers and bushings, are considered to be among the most critical elements of almost any electrical power system. As a result, the continued, reliable performance of such equipment is essential to the efficient generation and transmission of electrical power. In addition, the catastrophic failure and resulting unavailability of oil-filled equipment can have serious, even life-threatening, consequences for end users and can result in a substantial loss of revenue to consumers and utilities. An unexpected power failure can also cause significant damage to peripheral operating equipment, such as electrical manufacturing devices, or result in collateral environmental damage, or require the use of emergency alternative power sources during and after the failure.

Thus, the early detection of incipient faults in oil-filled equipment used in the transmission or control of electrical power, such as transformers and shunt reactors, can have a significant, measurable impact on end users and effect the overall reliability and profitability of electric utilities. The effective monitoring of electrical equipment performance levels to detect faults also provides end users with the opportunity to strategically plan and schedule power outages or routine maintenance, and thereby better manage power equipment utilization and its availability in specific geographic markets. The total operating costs for electrical grids can also be significantly reduced if the utility uses equipment that can be repaired within a scheduled repair plan or can be taken out of service at the first sign of trouble before a catastrophic failure occurs.

For many years, electric utilities have recognized the need to monitor the performance level over extended periods of time of critical pieces of power equipment in order to extend the useful life of the equipment and prevent catastrophic failures. Various insulating dielectric fluids (typically consisting of one or more chemically stable hydrocarbon fluids) have been used in the past with transformers and other like equipment to electrically isolate the transmission subsystems. Dielectric oil and solid cellulose dielectric materials are perhaps the best known insulating materials used for such purposes. Even during normal operating conditions, these insulating materials tend to degrade and break down under the inherent thermal and electrical stresses in the system. The degradation process creates by-product gases (generally low molecular weight hydrocarbons) of varying composition and different concentrations, depending on the severity and duration of the electrical stresses placed on such materials. Even under normal operating conditions, a small, but stable amount of gas and water vapor are produced during degradation.

That is, it is known that a measurable portion of the by-product gases dissolve in the dielectric oil at a given operating temperature and pressure and that data reflecting the nature and amount of individual gases sampled during operation can be used to identify the type and severity of the corresponding electrical fault in the equipment (such as a transformer malfunction). Even minute detected changes in the chemical composition of the gas produced and the rate of gas production over time can be important factors in determining the type of fault(s) involved, the evolution of the fault(s) and the potential consequences to related pieces of equipment. Thus, the detection of certain types of gas compounds can be correlated with known electrical faults. If rapid overheating or arcing occurs in the system, a substantial amount of gases and water vapor will be produced in a short period of time. Typically, the hydrocarbon-based dielectric oil produces free hydrogen, hydrocarbons, carbon dioxide and/or carbon monoxide gases as it thermally degrades ("breaks down"), while most dielectric paper substrates produce only carbon monoxide, carbon dioxide and water.

Because different dissolved gases and vapor (which typically includes water) indicate developing faults in the equipment, the dissolved gas data can be used to predict future faults and changing operating conditions. Thus, as noted above, accurate measurements of the levels of dissolved gases and/or vapor on a real time basis can be critical to understanding and predicting the health of an entire, integrated electrical network and can help identify electrical problems that arise before a catastrophic failure ensues.

The degradation of conventional dielectric oils normally produces hydrogen, methane, ethane, ethylene and acetylene in gas form. Any overheating of oil due to partial electrical discharges or partial arcing will produce one or more of those gases in varying amounts under different operating conditions. "Hot spots" in the equipment can often cause portions of the dielectric oil to overheat, producing primarily ethylene and measurable concentrations of hydrogen. Partial electrical discharges typically produce only hydrogen and methane. More severe arcing, on the other hand, can result in higher concentrations of hydrogen and acetylene which increase in amount as the oil fault temperature increases. Certain gases are known to be associated with each type of fault. Thus, the detection of individual gases and the rate of degradation depend on the type of dielectric, the nominal temperature of the oil at the point of degradation and the amount of heat energy being released into the oil at the fault location (the "hot spot").

In like manner, the thermal degradation of oil-impregnated cellulose materials produces different amounts of carbon monoxide, carbon dioxide and water, depending on the dielectric involved, the amount of heat generated and nominal operating conditions. Similar "hot spots" in windings, insulated leads and areas where pressboard and cellulose components and spacers are used also produce gases during degradation. Again, these hot spots tend to be localized and decompose the solid insulation in the specific areas of electrical stress.

In the past, users of electrical equipment, particularly transformers, have attempted to monitor and predict failures by manually taking samples from the insulating fluids at prescribed time intervals and then analyzing the samples at a location remote from the equipment itself. Free gases were also extracted from the "head space" of the transformer or other equipment using known sampling techniques and then injected into a gas chromatograph in order to determine the concentration and identity of the components in the extracted material. This procedure might be repeated several times a day to determine trends in the concentration of gases dissolved in the fluid. If the equipment owner failed to periodically test for rising levels of dissolved gases and water vapor in the head space, or misread or overlooked the data, the associated electrical equipment could fail, resulting in costly replacement and general power deterioration and/or outages. The degradation caused by electrical faults can occur very quickly. Thus, even sporadic sampling at prescribed time intervals is not effective in preventing significant damage to a transformer or downstream equipment.

Thus, for many years a significant need has existed for a reliable and cost-effective method and an apparatus capable of continuously and quantitatively detecting and measuring the concentration of selective dissolved gas and/or vapor components in fluids used to insulate electrical equipment.

Most electric utilities in the United States still use some form of periodic dissolved gas analysis (like DGA), with scheduled sampling, chromatographic analysis in the laboratory and fault diagnosis in order to identify and predict failure conditions of transformers. A clear need exists therefore for a method to detect and monitor a change in fault gases on a continuous basis, for example in a manner capable of linking individual DGA events. There are many well-documented cases of a critical power transformer failing catastrophically within days or even hours after being energized and/or after the onset of an increasing change in gas production due to oil degradation. With short fault development periods it is impractical, if not impossible, to identify serious faults with an annual or semi-annual monitoring event.

The present invention offers a significant improvement over prior art detection and monitoring equipment by providing a method and apparatus for the continuous detection and analysis of incipient electrical faults in transformers and like equipment. The disclosed method and apparatus will also substantially reduce, if not eliminate, unplanned power outages of transformers and other equipment, thereby improving the overall reliability of power grids and power transmission to end users.

The present invention also represents a cost-effective and more reliable apparatus and method for quantitatively determining the concentrations of certain dissolved and vapor phase constituents resulting from the expected degradation of dielectric fluids, and for making such quantitative determinations on a substantially real time, i.e., continuous basis. Because even minor electrical fault conditions can lead to catastrophic failures of downstream equipment, the method and apparatus according to the invention allow for early fault detections while providing continuous information regarding detected faults, including alarms, to end users such as substation personnel, thereby enhancing the overall safety of the personnel and protecting the operating integrity of downstream equipment. Also disclosed is the preferred means for detecting rapidly developing electrical faults on a real time basis and providing emergency information to end users who can then marshal the resources necessary to reduce or prevent potential damage to other power equipment.

BRIEF SUMMARY OF THE INVENTION

The present invention satisfies a significant need in the electrical field by providing a novel means for detecting, analyzing and monitoring the levels of certain dissolved gases and/or vapor components (including water vapor) of an insulating fluid. The present invention also provides means for measuring the concentration of the by-products of degradation on a continuous, substantially real-time basis and then evaluating the measured data in order to determine current equipment performance and prevent future equipment failures.

The present invention utilizes a continuous flow design capable of providing constant, updated information regarding the specific concentration of selected dissolved gases and/or vapor. The apparatus according to the invention is capable of detecting and analyzing up to three different components simultaneously and supplying accurate numeric concentration levels for each component. If the concentration of gases and/or vapor rises quickly or approaches a hazardous level, an alarm can also be triggered based on the detected data.

The concentrations of gases and water vapor in the dielectric fluid are calculated by the concentrations of the gases and water vapor in the extracted gas phase using known solubility coefficients. The gas membrane extraction process itself is dynamic in nature. That is, gases can permeate in either direction across the barrier, thereby allowing for measurements of decreasing concentrations as well as increasing concentrations.

The preferred method for analyzing and measuring the gas and/or vapor components in an insulating fluid according to the present invention includes the following basic steps:

passing a fluid by one side of a membrane to extract the dissolved gas and/or vapor components from the fluid;

analyzing the gas and/or vapor in an infrared gas cell detection system to determine the identity and concentration of the components; and recirculating the gases and/or vapor back to the extraction unit to maintain equilibrium across the membrane.

The preferred embodiment of the invention includes an apparatus for implementing the above described method, that includes:

a gas extractor unit for separating the gases and/or vapor (including water) from the fluid, comprising a gas-permeable membrane and a small gas chamber with one gas stream inlet and one gas stream outlet;

an infrared gas analyzer for determining the component concentration, comprising a collimated infrared source, a gas cell with gas inlet and outlet at both ends, a quad detector with integral optical infrared filters, an infrared source controller, and a detector signal processor; and a gas pump for circulating the extracted gases and/or vapor from the gas chamber to the gas analyzer in a closed loop.

In the preferred embodiment, the system analyzes two gases, ethylene and carbon monoxide, and one vapor, water. The detection limits are 6 parts per million (v/v) for ethylene; 5 parts per million (v/v) for carbon monoxide; and 5% Relative Humidity for water. The nominal insulating oil is conventional transformer oil and the membrane preferably consists of fluorosilicone or perfluoro polymer. The system can be expanded to monitor additional gases and/or vapor components.

DETAILED DESCRIPTION OF THE INVENTION

Figure 1:
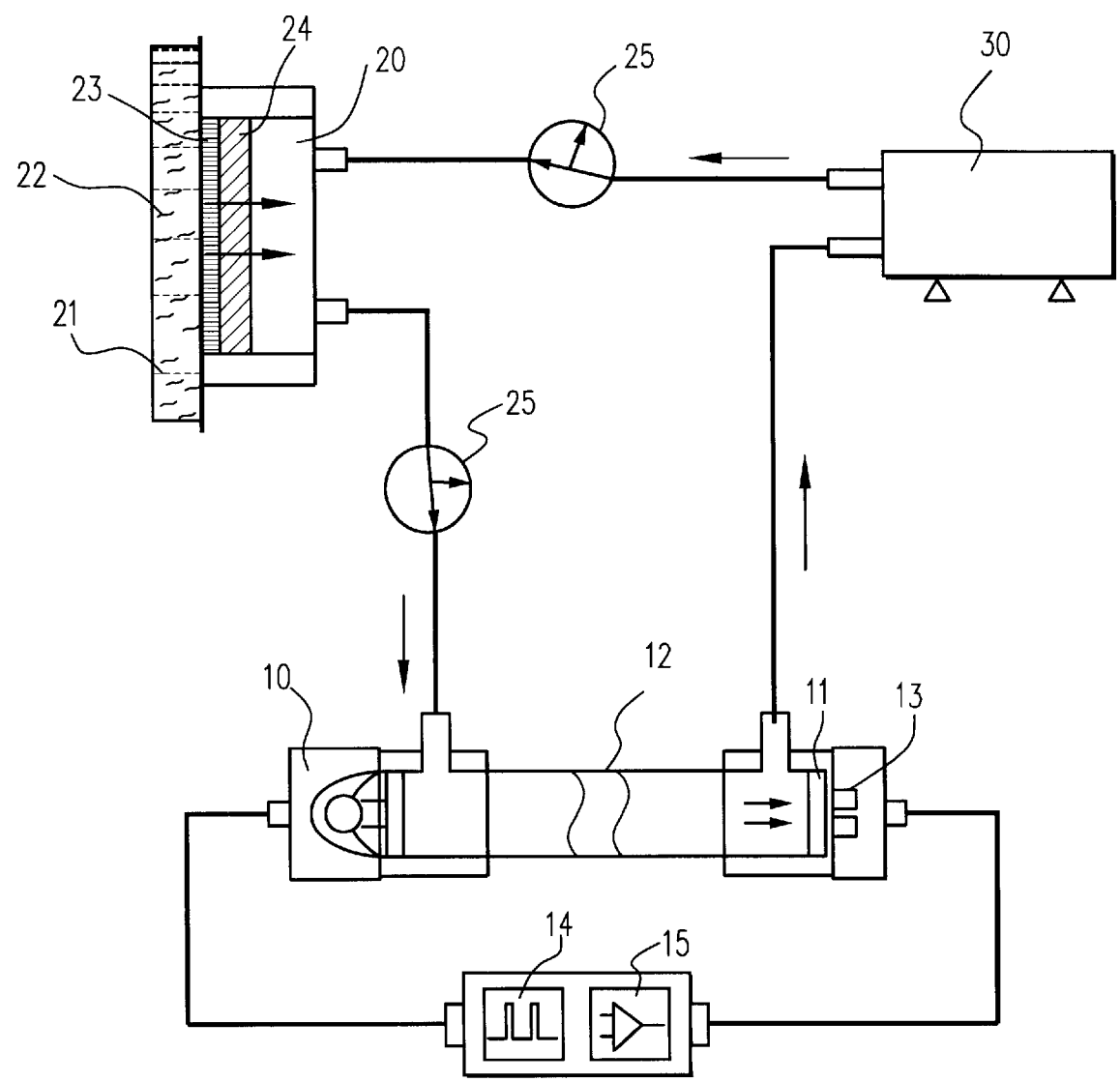
FIG. 1 of the drawings illustrates the preferred apparatus according to the invention for continuously detecting and analyzing volatile substances dissolved in insulating fluid in accordance with the invention, i.e., a continuous gas and/or vapor cycle that includes an extraction unit, analysis unit and gas pump.

FIG. 1 depicts both an apparatus diagram and flow chart showing the preferred apparatus and the steps for monitoring the performance level of electrical equipment containing insulating fluids in accordance with the invention. A typical embodiment includes three basic stations—a gas membrane extraction unit, an infrared analysis unit, and a gas recycle pump.

As discussed above, electrical and thermal stresses resulting from arcing or other electrical faults in the system tend to break down insulating fluid 21, creating immediate "hot spots" within the fluid and generating gases and water vapor 22 that dissolve in the dielectric fluid in amounts that vary over time depending on the severity of the stresses. The gas and/or vapor rich fluid flows by the gas extraction cell 20 (also referred to herein as a "gas extractor"). The gas extraction cell 20 contains a polymer membrane 23 through which the gases and water vapor permeate. The insulating fluid itself does not pass through polymer membrane 23 which is a highly permeable, but oil resistant, material such as fluorosilicone or perfluoro polymer. The membrane is supported by a stainless steel frit disk 24. The frit disk can be constructed using a known sintering process that renders the metallic parts porous. Due to its porous structure, the support disk does not create any significant restriction to the passage of gas and/or vapor through the membrane.

The extracted gases and/or vapor flow to an infrared gas analyzer which determines the identity and concentration of components using an infrared source 10, a gas cell 12, a quad detector 13 having a plurality of optical infrared filters, an infrared source controller 14, and a detector signal processor 15. The gases to be analyzed pass through an IR transparent window 11 directly into the quad detection unit 13. The preferred system uses a DC voltage of 15V±1% and a maximum DC current of 3 amperes.

The infrared source 10 is collimated in design and thus has a relatively long focal length. The preferred infrared source is also electronically pulsable, with the power level and frequency of pulses being controlled by an electronic controller 14. The pulsable system may be powered on and off without damaging the infrared source, thereby eliminating the need for a mechanical "chopper" that might otherwise be required for non-pulsable systems. This also reduces the number of mechanical moving parts, making the system more reliable over extended periods of use.

The infrared source 10 has a relatively high IR energy throughput with a typical minimum source power of 1.5 Watts and a maximum source power of 3 Watts, ensuring a relatively high signal-to-noise ratio. The detection levels of the gases and/or vapor in the system are in the parts per million range. Thus, it is critical that the amount of noise be minimized to maintain high resolution and high detectability. The signal-to-noise ratio is a function of source temperature, pulsing efficiency, and the amount of energy that reaches the detector. In the preferred embodiment, the infrared source has a modulation frequency of 2 to 12 Hz and a duty cycle of 25%.

Gas cell 12 consists of a cylindrical metal tube with mechanical supports at both ends, as well as infrared transparent windows 11, a gas port and an o-ring. The metal tube is preferably made of anodized aluminum or other surface treated aluminum. An anodized aluminum tube is strong, non-corrosive, and easy to handle. The windows preferably consist of a barium fluoride crystal and are transparent to infrared light. The o-ring should preferably be made of viton rubber.

Quad detector 13 utilizes four narrow bandpass filters, each having a specified wavelength that corresponds to a specific gas or vapor components. (See Table 1 below for the properties of representative sample filters). Nominally, the filters are 2 mm×2 mm in size and mounted with epoxy in a quadrature pattern. The filters are positioned between a broad bandpass filter window and a pyroelectric device comprising four elements made of lithium tantalate crystals heat sunk mounted to a transistor header. The elements detect very small heat increments and are positioned within the detector for rapid heat dissipation during operation.

TABLE 1

Properties of Sample Bandpass Filters

| Number | Target gas | Wavelength (microns) | FWHM bandwidth (micron) | Thickness (mm) | Dimension (mm × mm) |
|---|---|---|---|---|---|
| 1 Narrow | Ethylene | 10.53 | 0.050 | 1 | 2 × 2 |
| 2 Narrow | Carbon Monoxide | 4.6 | 0.023 | 1 | 2 × 2 |
| 3 Narrow | Water | 6.6 | 0.033 | 1 | 2 × 2 |
| 4 Narrow | Reference | 8.9 | 0.045 | 1 | 2 × 2 |
| 5 Broad | Window | 1–13 | | 1 | 6 × 6 |

In operation, the infrared source controller 14 constantly adjusts the input power level of the infrared energy source to a fixed value. Controller 14 also maintains the frequency of the pulsation, preferably between 2 and 12 Hz.

The detector signal processor 15 includes a microprocessor that amplifies and filters the signal received from the detector. The processor depicted in FIG. 1 does not calculate the concentration of the dissolved components in the dielectric fluid. The program could be designed to simultaneously perform that data calculation, however, depending on the preferred system requirements. The data processed in the embodiment of FIG. 1 is transferred to a separate computer or PLC (Programmable Logic Controller) located, for example, in a control room or in a separate control cabinet that handles the data acquisition, data processing and control functions.

The four channels available in the processor operate with three levels of diagnostic to ensure that the gas analyzer is functioning properly. The first diagnostic level continuously monitors all of the on board DC power supplies by comparing the internal voltage of the microprocessor to a separate external reference voltage for the gas analyzer. If the voltage falls outside a prescribed range, a fault condition arises (for example, when the power supply fails) and prevents further testing. A second level of diagnostics measures the null and gain circuits using dedicated voltage inputs. The third level of diagnostics tests the signal conditioning circuitry using an analog switch that changes the signal path from monitoring the detector outputs to monitoring a fixed test signal.

As FIG. 1 illustrates, the gas being tested flows from the gas extraction cell to diaphragm gas pump 30. The pump continuously circulates the extracted and analyzed gases and/or vapor in a closed loop back to the extraction unit.

The entire system must be periodically adjusted to zero operation in order to calibrate the infrared source, detector and associated electronics. The infrared source material could slowly wear out over time and therefore a new zero point must be set after a certain period of continuous use.

The system can be electronically calibrated by opening the two three-way valves 25 and pumping pure air into the system. This ensures that no gas or water vapor from the insulating fluid is present during the calibration step. The infrared source controller is then adjusted to ensure that the detection level is set to zero.

While the above invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. An apparatus for continuously analyzing and measuring the contents of gas and/or vapor components in an insulating fluid substantially on a real time basis, comprising:

a gas extractor unit for separating the gases and/or vapor from the fluid, comprising a gas and/or vapor permeable polymer membrane and a gas chamber with one gas stream inlet and one gas stream outlet;

an infrared gas analyzer for determining the concentration of individual gas or vapor components, comprising a collimated infrared source, a gas cell with a gas inlet and outlet at both ends, a quad detector having ultra narrow band optical infrared filters, each filter having a specified wavelength corresponding to said individual gas or vapor components, an infrared source controller having means for continuously adjusting the output power level of the infrared energy source to a fixed value, and a pyroelectric detector signal processor;

a gas pump for recycling the gases and/or vapor to said gas extractor in a closed loop; and calibration means for said infrared gas analyzer including valve means for purging the gas and/or vapor components using air and resetting said collimated infrared source to zero.

2. An apparatus as claimed in claim 1, wherein said fluid is an insulating fluid.

3. An apparatus as claimed in claim 1, wherein said fluid is transformer oil.

4. An apparatus as claimed in claim 1, wherein said gases and vapor are formed from the break down of the fluid and insulating paper.

5. An apparatus as claimed in claim 1, wherein said gases are from the group of ethylene, carbon dioxide, acetylene, methane, and carbon monoxide.

6. An apparatus as claimed in claim 1, wherein said vapor is water.

7. An apparatus as claimed in claim 1, wherein said membrane is a highly permeable and oil resistant polymer.

8. An apparatus as claimed in claim 1, wherein said membrane is fluorosilicone or perfluoro polymer.

9. An apparatus as claimed in claim 1, wherein said membrane is supported by a stainless steel sintered frit disk.

10. An apparatus as claimed in claim 1, wherein said gas cell is an anodized aluminum tube.

11. An apparatus as claimed in claim 1, wherein the gas cell mechanical support windows are made of barium fluoride crystal.

12. An apparatus as claimed in claim 1, wherein said quad detector comprises four narrow bandpass filters, each having a specified wavelength that corresponds to a specific gas or vapor.

13. An apparatus as claimed in claim 12, wherein said filters are placed between a broad bandpass filter and a pyroelectric device.

14. An apparatus as claimed in claim 13, wherein said pyroelectric device has four elements made of lithium tantalate crystals that are heat sunk mounted to a transistor header.

15. An apparatus as claimed in claim 1, wherein said infrared source controller maintains the pulse frequency between 2 and 12 Hz.

16. An apparatus as claimed in claim 1, wherein said detector signal processor is a microprocessor that simultaneously amplifies, filters and balances the output signal from the detector.

17. An apparatus as claimed in claim 2, wherein said quad detector includes a pyroelectric crystal covered with an optical filter that only allows non-absorption IR band to pass.

18. A method for continuously detecting, analyzing and measuring, on a real time basis, the concentration of dissolved gases and/or vapor components in dielectric fluids used to insulate electrical equipment, comprising:

passing a dielectric fluid containing dissolved gasses and/or vapor components by a gas extractor and exposing the dissolved gasses and/or vapor components to one side of a polymer membrane, said membrane being highly permeable to the dissolved gases and/or vapor components but impermeable to the dielectric fluid;

passing said gasses and/or vapor components into an extraction chamber within said gas extractor to thereby isolate said gases and/or vapor components from said dielectric fluid;

feeding a portion of said extracted and isolated gases and/or vapor components within said extraction chamber into an infrared gas detection device;

analyzing on a real time basis said portion of said extracted and isolated gases and/or vapor components to determine the identity and relative concentration of individual gas constituents;

determining the relative concentration of the same individual gas constituents within said extraction chamber based on an analysis of said portion of said extracted and isolated gases and/or vapor components;

recycling the analyzed gases and/or vapor components back to said gas extractor in a closed loop in order to maintain a dynamic equilibrium of gases and vapor across said polymer membrane; and periodically calibrating said infrared gas detection device by pumping air into the system to purge the extracted gases or vapor and thereafter adjusting said infrared gas detector.

19. A method according to claim 18, further comprising the step of triggering an alarm based on the detected and analyzed data if the concentration of gases and/or vapor rises too quickly or the concentration approaches a hazardous level.

20. A method according to claim 18, wherein said step of analyzing a portion of said extracted and isolated gases detects the presence and concentration of ethylene, carbon monoxide and water vapor.

21. A method according to claim 20, wherein said step of analyzing said portion of extracted and isolated gases detects the presence and concentration of gases up to 6 parts per million (v/v) for ethylene, 5 parts per million (v/v) for carbon monoxide and 5% relative humidity for water vapor.

22. A method according to claim 18, wherein said step of passing said dissolved gasses and/or vapor components through said polymer membrane polymer uses a membrane consisting of fluorosilicone or perfluoro polymer.

* * * * *